(12) United States Patent
Brieva et al.

(10) Patent No.: US 8,486,463 B1
(45) Date of Patent: Jul. 16, 2013

(54) COSMETIC COMPOSITION COMPRISING ALOE VERA AND CAPRYLYL SALICYLIC ACID AND METHOD OF MAKING

(75) Inventors: Patricia Brieva, Manalapan, NJ (US); Angelike Galdi, Westfield, NJ (US); Natver Mehta, Lake Hopatcong, NJ (US); Jim M. Singer, South Orange, NJ (US); Lindsay Menzer, Bedminster, NJ (US); Michell Chen, Edison, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/467,507

(22) Filed: May 9, 2012

(51) Int. Cl.
*A61K 36/886* (2006.01)
*A61K 36/00* (2006.01)

(52) U.S. Cl.
USPC .......................................... 424/744; 424/725

(58) Field of Classification Search
None
See application file for complete search history.

(56) References Cited

U.S. PATENT DOCUMENTS

| 2005/0118285 A1 | 6/2005 | Lacoutiere |
| 2007/0027223 A1 | 2/2007 | Bruchert et al. |
| 2011/0045037 A1 | 2/2011 | Tamarkin et al. |
| 2011/0311470 A1 | 12/2011 | Cherette et al. |

FOREIGN PATENT DOCUMENTS

WO 2004064833 A1 8/2004

*Primary Examiner* — Qiuwen Mi
(74) *Attorney, Agent, or Firm* — McNees Wallace & Nurick LLC

(57) ABSTRACT

A cosmetic composition in the form of an emulsion and process for preparing the cosmetic composition using cold-processing are provided. The cosmetic composition includes at least one hydrating agent including Aloe Barbadensis Leaf Juice, the hydrating agent at a concentration, by weight, of about 10% to about 70%, based upon weight of the composition. The composition includes at least one viscosity modifier, at least one mattifer, at least one humectant, at least one thickener, and caprylyl salicylic acid. The caprylyl salicylic acid is at a concentration, by weight, of about 0.01% to about 0.5% based upon weight of the composition. The cosmetic composition has a hydration index greater than water.

19 Claims, No Drawings

COSMETIC COMPOSITION COMPRISING ALOE VERA AND CAPRYLYL SALICYLIC ACID AND METHOD OF MAKING

FIELD OF THE INVENTION

The present invention is directed to cosmetic compositions and methods of producing cosmetic compositions. More specifically, the present invention is directed to a cosmetic composition including at least one hydrating agent, aloe vera, a viscosity modifier, a thickener, a mattifier, a humectant, and caprylyl salicylic acid.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous-dispersing-continuous phase and an oily-dispersed-discontinuous phase, or of an emulsion of the water-in-oil (W/O) type consisting of an oily-dispersing-continuous phase and an aqueous-dispersed-discontinuous phase. O/W emulsions are preferred in the cosmetics field, because O/W emulsions comprise an aqueous phase as external phase, which gives the emulsions, when applied to the skin, a fresher, less greasy and lighter feel than W/O emulsions.

Challenges have been encountered in obtaining O/W emulsions including Aloe Barbadensis Leaf Juice or aloe vera compared to O/W emulsions including water. One of the reasons for difficulty in forming O/W emulsions including aloe vera is that aloe vera has different properties than water. More specifically, aloe vera has a different pH, has a different surface tension, and also includes amino acids that are not present in water. The surface tension of water is 55.73 dyne/cm and a pH of 7, based on temperature and purity level. In contrast, the surface tension of aloe vera is ~49.75 dyne/cm and pH is 4, based on temperature and purity level. The different material strength of aloe vera, compared to water, results in a lower surface tension, making it harder to include in cosmetic formulations such as O/W emulsions. The amino acids present in aloe vera increase the difficulty in suspending aloe vera particularly when the aloe vera is not suspended by heated emulsifiers and surfactants. Heating destroys and degrades some of the amino acids in the aloe vera, thereby decreasing the healing properties of aloe vera.

Most cosmetic compositions include preserving agents having antibacterial properties. Use of parabens as a preserving agent has received consumer scrutiny; however, paraben-free systems are difficult to formulate because paraben-free systems use preservatives that reduce emulsion stability and decrease viscosity of formulations.

A cosmetic composition and method of producing cosmetic compositions that do not suffer from one or more of the above drawbacks would be desirable in the art.

BRIEF DESCRIPTION OF THE INVENTION

In an exemplary embodiment, a cosmetic composition is provided. The cosmetic composition includes at least one hydrating agent including Aloe Barbadensis Leaf Juice, the hydrating agent at a concentration, by weight, of about 10% to about 70%, based upon weight of the composition. The composition includes a viscosity modifier, a mattifer, a humectant, at least one thickener, and caprylyl salicylic acid. The caprylyl salicylic acid is at a concentration, by weight, of about 0.01% to about 0.5% based upon weight of the composition. The cosmetic composition has a hydration index greater than water.

The present disclosure is also directed to a method for cosmetic treatment of keratinous tissues by applying the above-disclosed composition onto a surface of the keratinous tissue.

In another exemplary embodiment, a process for preparing the cosmetic composition is provided. The process includes mixing a first phase including the at least one hydrating agent including Aloe Barbadensis Leaf Juice, a viscosity modifier, a mattifer, and a humectant. The process includes mixing a second phase including the at least one thickener and caryloyl salicylic acid at ambient temperature. The process includes homogenizing the mixed first phase and the mixed second phase forming an oil-in-water emulsion at ambient temperature. During the process, the temperature of the composition during mixing and homogenizing does not exceed about 30° C.

Other features and advantages of the present invention will be apparent from the following more detailed description of the preferred embodiment which illustrates, by way of example, the principles of the invention.

DETAILED DESCRIPTION OF THE INVENTION

"Keratinous tissue," as used herein, includes but is not limited to skin, hair, and nails.

"Homogenous" means substantially uniform throughout, i.e., a single phase mixture.

In the present application the term "ambient temperature" means a temperature of about 25° C.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratinous tissue.

It has been surprisingly discovered by the inventors that high levels of aloe vera, a viscosity modifier, at least one thickener, a mattifier, a humectant, and caprylyl salicylic acid can be formulated as an emulsion using cold processing methods at ambient temperatures. Additionally, it has been surprisingly discovered by the inventors that the composition of the present disclosure can be formulated as a mousse having a desired foam structure with reduced tackiness and a hydration index greater than water.

Hydrating Agent

The hydrating agent is at a concentration, by weight, of about 0.1% to about 70%, or alternatively about 10% to about 60% or alternatively about 25% to about 50%, based upon weight of the composition. In one embodiment, the hydrating agent is aloe vera (INCI: Aloe Barbadensis Leaf Juice), water, and combinations thereof.

The Aloe Barbadensis Leaf Juice and water are advantageously present at a concentration ratio, by weight, of about 10:90 to about 90:10, or alternatively about 20:80 to about 80:20, or alternatively about 30:70 to about 70:30, based upon weight of the at least one hydrating agent. In one embodiment, a 50:50 ratio of Aloe Barbadensis Leaf Juice to water, based upon weight of the at least one hydrating agent is preferred.

The concentration of Aloe Barbadensis Leaf Juice is advantageously present at a concentration, by weight, of about 10% to about 50%, or alternatively about 15% to about 45%, or alternatively about 20% to about 40%, based upon weight of the composition.

In a preferred embodiment, the Aloe Barbadensis Leaf Juice used is 30% Aloe Vera Gel (1×) Decolorized from Terry Laboratories, Melbourne, Fla.

Viscosity Modifier

The viscosity modifier present in the cosmetic composition according to the present disclosure includes xanthan gum, carrageenan gum, guar gum, and combinations thereof.

The viscosity modifier is advantageously present at a concentration, by weight, of about 0.01% to about 2%, or alternatively about 0.05% to about 1.8%, or alternatively about 0.1% to about 1.5%, based upon weight of the cosmetic composition.

Humectant

The humectant present in the cosmetic composition according to the present disclosure includes glycerin, sodium hyaluronate, panthenol, urea, hydroxyethyl urea, PEG/PPG/polybutylene glycol-8/5/3 glycerin, hydrolyzed hyaluronic acid, niacinamide, mannose, myristyl malate phosphonic acid, biosaccharide gum, and combinations thereof.

The humectant is advantageously present at a concentration, by weight, of about 0.01% to about 30%, or alternatively 0.1% to alternatively about 25%, or alternatively about 1% to about 20%, based upon weight of the cosmetic composition.

Mattifier

The mattifier present in the cosmetic composition according to the present disclosure includes methyl methacrylate/glycol dimethacrylate crosspolymer, vinyl dimethicone/methicone silsesquioxane crosspolymer, methyl methacrylate crosspolymer, polyamides, nylon-12, polyethylene, talc, titanium dioxide, silica, aluminum starch octenylsuccinate, and combinations thereof.

In a preferred embodiment, the mattifier is MICROSPONGE® 5640 (methyl methacrylate/glycol dimethacrylate crosspolymer) available from Amcol, Lafayette, La. In another preferred embodiment, the mattifier is KSP 100 (vinyl dimethicone/methicone silsesquioxane crosspolymer) available from Shin Estu, East Nassau N.Y.

In the cosmetic composition of the present disclosure, the mattifier acts as a vehicle delivery system, an oil absorber, and to improve the sensory feel, reducing tackiness of the cosmetic composition.

The mattifier is advantageously present at a concentration, by weight, of about 0.05% to about 5%, or alternatively about 0.1% to about 3%, or alternatively about 0.2% to about 2%, based upon weight of the cosmetic composition.

Aluminum Starch Octenylsuccinate

The cosmetic composition further includes comprising aluminum starch octenylsuccinate. In a preferred embodiment, the aluminum starch octenylsuccinate is DRY FLO® PLUS starch, available from Akzo Nobel, Chicago, Ill.

In the cosmetic composition of the present disclosure, the aluminum starch octenylsuccinate acts as a detackifier.

The aluminum starch octenylsuccinate is advantageously present at a concentration, by weight of about 0.1% to about 10%, or alternatively about 0.5% to about 8%, or alternatively about 1.0% to about 5%.

Thickener

The at least one thickener present in the cosmetic composition according to the present disclosure includes acrylates/C10-30 alkyl acrylate crosspolymer, sodium acrylate/sodium acryloyldimethyl taurate copolymer, acrylamide/sodium acryloyldimethyltaurate copolymer, ammonium polyacryloyldimethyl taurate, ammonium acryloydimethyl taurate/VP copolymer, carbomer, xanthan gum, sodium polyacrylate, and combinations thereof.

The thickener is advantageously present at a concentration, by weight, of about 0.01% to about 2%, or alternatively about 0.08% to about 1.5%, or alternatively about 0.1% to about 1.0%, based upon weight of the cosmetic composition.

Caprylyl Salicylic Acid

Caprylyl salicylic acid is present in the cosmetic composition and is desquamation cell turnover active or skin conditioning agent. Caprylyl salicylic acid is typically challenging to include in emulsions because the caprylyl salicylic acid is prone to precipitate out and crystallize if the correct solvent system is not used.

The caprylyl salicylic acid is advantageously present at a concentration, by weight, of about 0.01% to about 0.5%, or alternatively about 0.03% to about 0.4%, or alternatively about 0.05% to about 0.3%, based upon weight of the cosmetic composition.

Aerosolizing Agent

The cosmetic composition of the present disclosure optionally includes at least one aerosolizing agent to create a mousse having desired foam structure with reduced tackiness. The cosmetic composition includes dimethyl ether, isobutane and butane, isobutene and propane, and combinations thereof.

The aerosolizing agent is advantageously present at a concentration, by weight, of about 0.1% to about 10%, or alternatively about 0.5% to about 9%, or alternatively about 1% to about 8%, based upon weight of the cosmetic composition.

In one embodiment, the aerosolizing agent is a mixture of dimethyl ether and any combination of isobutane, butane and propane. In a preferred embodiment the aerosolizing agent has about 50:50 mixture of dimethyl ether and A-46 propellant (mixture of isobutane and propane), available from AVANTEC (SOTRAGAL), France.

The cosmetic composition of the present disclosure is paraben free.

The cosmetic composition of the present disclosure includes less than about 3%, by weight, of surfactants and emulsifiers, based upon weight of the composition.

The cosmetic composition of the present disclosure has a viscosity at 25° C. of 25 milli-Pascal·seconds (mPa·s) to about 105 mPa·s, or alternatively about 40 mPa·s to about 95 mPa·s, or alternatively about 65 mPa·s to about 85 mPa·s. The viscosity was measured with a Viscometer Rheomat at 25° C. The viscosity of the emulsions was measured with Spindle No. 3 at 200 rpm rotations per min at 25° C. for 10 minutes.

The cosmetic composition of the present disclosure forms an oil-in-water type emulsion using cold-processing methods and without the use of heat.

Aqueous Phase

The aqueous phase present in the cosmetic composition according to the disclosure includes water, Aloe Barbadensis Leaf Juice, at least one viscosity modifier, at least one mattifier, and at least one humectant. Suitable viscosity modifiers for the aqueous phase include, but are not limited to, xanthan gum, carrageenan gum, guar gum, and combinations thereof. Suitable mattifiers for the aqueous phase include, but are not limited to, methyl methacrylate/glycol dimethacrylate crosspolymer, vinyl dimethicone/methicone silsesquioxane crosspolymer, methyl methacrylate crosspolymer, nylon-12, polyamides and combinations thereof. Suitable humectants include, but are not limited to, glycerin, sodium hyaluronate, panthenol, and combinations thereof.

Oil Phase

The oil phase present in the composition according to the disclosure includes dimethicone, at least one thickener, and caprylyl salicylic acid. Suitable thickeners include, but are not limited to, acrylates/C10-30 alkyl acrylate crosspolymer, sodium acrylate/sodium acryloyldimethyl taurate copolymer, acrylamide/sodium acryloyldimethyltaurate copolymer, ammonium polyacryloyldimethyl taurate, ammonium acryloydimethyl taurate/VP copolymer, and combinations thereof.

The composition of the present disclosure may also contain cosmetically acceptable additives or adjuvants as well as cosmetic or dermatologic active agents. Representative additives and adjuvants include, for example, water-soluble or water-miscible solvents or co-solvents, dispersion enhancing agents, moisturizers, colorants, fillers, preservatives, antioxidants (e.g., EDTA, BHT, tocopherol), essential oils, fragrances, dyes, neutralizing or pH-adjusting agents (e.g., triethylamine (TEA) and sodium hydroxide), conditioning or softening agents (e.g., panthenol, allantoin and glycerin) and extracts such as botanical extracts. Additives and adjuvants may be present in the compositions in amounts generally ranging from about 0.01% to about 10% by weight. Examples of cosmetic active agents or dermatological active agents include sunscreen agents (e.g., inorganic sunscreen agent, such as titanium dioxide and zinc oxide and organic sunscreen agents, such as octocrylene, ethylhexyl methoxycinnamate, and avobenzone), free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the cosmetic composition (i.e., aqueous and/or fatty (oil) phase).

Process

The process for preparing the cosmetic composition of the present disclosure, according to one embodiment, includes creating a stable oil-in-water emulsion without heating. The process uses a cold processing method which keeps the temperature below 30° C. and more preferably at ambient temperature during emulsification. The process includes mixing a first phase (aqueous) including at least one hydrating agent including Aloe Barbadensis Leaf Juice, at least one viscosity modifier, at least one mattifer, and at least one humectant at ambient temperature (about 25° C. and less than 30° C.). The process includes mixing a second phase (oily/fatty) including dimethicone, at least one thickener, and capryloyl salicylic acid at ambient temperature (about 25° C. and less than 30° C.). The process includes pouring the mixed second phase (oily/fatty) into the mixed first phase (aqueous). The process includes homogenizing the mixed first phase and the mixed second phase forming an oil-in-water emulsion without heat and at ambient temperature (about 25° C. and less than 30° C.). The process includes adding aluminum starch octenylsuccinate to the emulsion at ambient temperature (about 25° C. and less than 30° C.). After adding the aluminum starch octenylsuccinate, the composition is in the form of a liquid lotion having a hydration index greater than water and generally in the range of 100 to about 110. Optionally, an aerosolizing agent is added to composition. The liquid lotion composition is poured into an aerosol can and sealed with a dip tube. Next, the aerosolizing agent is added to the aerosol can containing the liquid lotion composition. The aerosolizing agent is added in a concentration, by weight, of about 0.1% to about 10%, based upon total weight of the composition.

Hydration Index

The cosmetic composition of the present disclosure has a hydration index of about 0.75 to about 1.2. In an embodiment, the cosmetic composition of the present disclosure has a hydration index greater than a formulation including only water.

The hydration index is calculated using the following equation $$IP_{1h} = \frac{\text{Average } [(T_{1h} - T_0)_{formula} - (T_{1h} - T_0)_{bare\ skin}]}{\text{Average } [(T_{1h} - T_0)_{reference} - (T_{1h} - T_0)_{bare\ skin}]}$$

where $IP_{1h}$ is the hydration index of the skin; $T_{1h}$ is the Corneometer reading one hour after applying the formula or reference, $T_0$ is the initial Corneometer reading right after applying the formula or reference, $(T_{1h}-T_0)_{formula}$ is the difference between the Corneometer reading one hour after applying the formula of the present disclosure to the skin and the Corneometer reading right after applying the formula of the present disclosure to the skin; $(T_{1h}-T_0)_{bare\ skin}$ is the difference between the Corneometer reading at the one hour mark and initial reading of bare skin; $(T_{1h}-T_0)_{reference}$ is the difference between the Corneometer reading one hour after applying the reference cream (containing 7% glycerin) to the skin and Corneometer reading right after applying the reference cream (containing 7% glycerin) to the skin. The Corneometer readings were taken at ambient temperatures. The Corneometer used to measure the hydration index was Corneometer® CM825, available from Courage+Khazaka, Köln, Germany.

The cosmetic composition of the present disclosure in any desirable cosmetic form, such as but not limited to, liquid lotions, creams, and mousses, can be applied to keratinous tissue to provide a greater hydration index than that of formulations containing only water with no aloe vera.

The following examples are intended to further illustrate the present invention. They are not intended to limit the invention in any way. Unless otherwise indicated, all parts are by weight.

EXAMPLES

TABLE 1

| Formulation | | Examples | |
|---|---|---|---|
| Phase | Ingredient (INCI Name) | 1 | 2 |
| A | Water | 29.016 | 58.776 |
| A | Aloe Barbadensis Leaf Juice | 29.76 | — |
| A | Xanthan Gum | 0.186 | 0.186 |
| A | Propylene Glycol | 5.58 | 5.58 |
| A | Caprylyl Glycol | 0.279 | 0.279 |
| A | Ethylhexylglycerin | 0.279 | 0.279 |
| A | Tetrasodium EDTA | 0.186 | 0.186 |
| A | Glycerin | 9.3 | 9.3 |
| A | Decyl Glucoside | 0.93 | 0.93 |
| A | Phenoxyethanol | 0.465 | 0.465 |
| A | Triethanolamine | 0.279 | 0.279 |
| A | Microsponge ® - Methylacrylate/Glycol Dimethacrylate Crosspolymer | 0.465 | 0.465 |
| B | Tocopherol | 0.093 | 0.093 |
| B | Hydrogenated Polyisobutene | 7.44 | 7.44 |
| B | Capryloyl Salicylic Acid | 0.093 | 0.093 |
| B | Polysorbate 80 | 0.093 | 0.093 |
| B | Acrylates/C10-30 Alkyl Acrylate Crosspolymer | 0.186 | 0.186 |
| B | Dimethicone | 4.65 | 4.65 |

TABLE 1-continued

| Formulation | | Examples | |
|---|---|---|---|
| Phase | Ingredient (INCI Name) | 1 | 2 |
| C | Aluminum Starch Octenylsuccinate | 3.72 | 3.72 |
| | Dimethyl Ether | 3.5 | 3.5 |
| | A 46 Isobutane (and) butane | 3.5 | 3.5 |
| | Total (wt/wt %) | 100 | 100 |
| | Type of composition | mousse | mousse |
| | Hydration Index before propellant | 1.07 | 1.04 |
| | Hydration Index after propellant | 0.93 | 0.92 |

Example 1 is a cosmetic compositon in the form of a mousse prepared according to the present disclosure including at least one hydrating agent including about a 50:50 ratio, by weight, of Aloe Barbadensis Leaf Juice and water, based upon weight of the at least one hydrating agent. The cosmetic composition includes a viscosity modifier, a mattifer, a humectant, at least one thickener, caprylyl salicylic acid, and aerosolizing agents. Example 2 is a reference example used to compare the hydration index of the present disclosure to that of a similar composition only containing water as the hydrating agent.

The mousse compositions, both Example 1 and Example 2, described above were prepared as follows. The ingredients of Phase A (aqueous phase) were added to a main kettle one at a time and mixed until uniform and dispersed. During addition of the ingredients and mixing, the main kettle and ingredients were kept at ambient temperature and did not exceed 30° C.

The ingredients of Phase B (oil/fatty phase) were added to a side kettle and mixed until uniform and dispersed. During addition of the ingredients and mixing, the side kettle and ingredients were kept at ambient temperature and the temperature of the ingredients did not exceed excessive temperatures due to mechanical shear. The contents of the side kettle were then added to the main kettle and emulsified for 15 minutes. Phase C, the aluminum starch octenylsuccinate was added to the kettle and mixed for 5 minutes to obtain a liquid lotion composition having a hydration index of 1.07 for Example 1 and hydration index of 1.04 for Example 2.

The liquid lotion composition was poured into an aerosol can, at a concentration of about 93% by weight, based upon weight of the composition, and sealed with a dip tube. Next, the aerosolizing agent at a concentration of about 7% by weight, based upon weight of the composition, was added to the sealed aerosol can. Next, the aerosol cans were purged with nitrogen and placed in a hot bath to determine if any leakage was present. The aerosol can were mounted with actuators. The aerosol cans were shaken, mixing the aerosolizing agent with the emulsion to provide a mousse.

The mousse of Example 1 has a desired foam structure with reduced tackiness and a hydration index greater than that of Example 2, which is a composition including only water and not aloe vera.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition in the form of an emulsion comprising:
    at least one hydrating agent including Aloe Barbadensis Leaf Juice, the hydrating agent at a concentration, by weight, of about 10% to about 70%, based upon weight of the composition;
    at least one viscosity modifier;
    at least one mattifer;
    at least one humectant;
    at least one thickener; and
    caprylyl salicylic acid, the caprylyl salicylic acid at a concentration, by weight, of about 0.01% to about 0.5% based upon weight of the composition,
    wherein the cosmetic composition has a hydration index greater than water.

2. The cosmetic composition of claim 1, further comprising an aerosolizing agent, the aerosolizing agent at a concentration, by weight, of about 0.1% to about 10%, based upon weight of the composition.

3. The cosmetic composition of claim 2, wherein the aerosolizing agent comprises dimethyl ether, isobutene and butane, isobutane and propane, or combinations thereof.

4. The cosmetic composition of claim 1, further comprising aluminum starch octenylsuccinate, the aluminum starch octenylsuccinate at a concentration, by weight of about 0.1% to about 5%.

5. The cosmetic composition of claim 1, wherein the at least one hydrating agent includes water.

6. The composition of claim 5, wherein the ratio of Aloe Barbadensis Leaf Juice to water is about 10:90 by weight to about 90:10 by weight, based upon weight of the at least one hydrating agent.

7. The cosmetic composition of claim 5, wherein the Aloe Barbadensis Leaf Juice is at a concentration, by weight, of about 10% to about 50%, by weight, based upon weight of the composition.

8. The cosmetic composition of claim 1, wherein the viscosity modifier comprises xanthan gum, carrageenan gum, guar gum, or combinations thereof.

9. The cosmetic composition of claim 1, wherein the viscosity modifier is at a concentration, by weight, of about 0.01% to about 2%, based upon weight of the composition.

10. The cosmetic composition of claim 1, wherein the mattifier comprises methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, or combinations thereof.

11. The cosmetic composition of claim 1, wherein the mattifier is at a concentration, by weight, of about 0.05% to about 5%, based upon weight of the composition.

12. The cosmetic composition of claim 1, wherein the humectant comprises glycerin, sodium hyaluronate, panthenol, urea, hydroxyethyl urea, PEG/PPG/polybutylene glycol-8/5/3 glycerin, hydrolyzed hyaluronic acid, niacinamide, mannose, myristyl malate phosphonic acid, biosaccharide gum, or combinations thereof.

13. The cosmetic composition of claim 1, wherein the humectant is at a concentration, by weight, of about 0.01% to about 30% by weight, based upon the weight of the composition.

14. The cosmetic composition of claim 1, wherein the at least one thickener comprises acrylates/C10-30 alkyl acrylate crosspolymer, sodium acrylate/sodium acryloyldimethyl taurate copolymer, acrylamide/sodium acryloyldimethyltaurate copolymer, ammonium polyacryloyldimethyl taurate, ammonium acryloyldimethyl taurate/VP copolymer, carbomer, xanthan gum, sodium polyacrylate or combinations thereof.

15. The cosmetic composition of claim 1, wherein the thickener is at a concentration, by weight, of about 0.01% to about 2%, based upon weight of the composition.

16. The cosmetic composition of claim 1, wherein the hydration index is about 0.75 to about 1.2.

17. A process for preparing the cosmetic composition according to claim 1, comprising:
   mixing a first phase including the at least one hydrating agent including Aloe Barbadensis Leaf Juice, a viscosity modifier, a mattifer, and a humectant;
   mixing a second phase including the at least one thickener and capryloyl salicylic acid at ambient temperature;
   homogenizing the mixed first phase and the mixed second phase forming an oil-in-water emulsion at ambient temperature; and
   wherein the temperature of the composition during mixing and homogenizing does not exceed about 30° C.

18. A process of claim 17, further comprising adding an aerosolizing agent after the step of adding aluminum starch octenylsuccinate.

19. A method for cosmetic treatment of keratinous tissues, comprising applying the cosmetic composition according to claim 1.

* * * * *